US005629209A

United States Patent [19]

Braun, Sr. et al.

[11] Patent Number: 5,629,209
[45] Date of Patent: May 13, 1997

[54] METHOD AND APPARATUS FOR DETECTING VISCOSITY CHANGES IN FLUIDS

[76] Inventors: Walter J. Braun, Sr., 7884 S. Argonne Ct., Aurora, Colo. 80016; Anthony A. Boiarski, 2615 Henthorn Rd., Upper Arlington, Ohio 43221; Walter J. Braun, Jr., 7884 S. Argonne Ct., Aurora, Colo. 80016; Steven P. Braun, 18824 N. 95th Ave., Peoria, Ariz. 85382

[21] Appl. No.: 545,523

[22] Filed: Oct. 19, 1995

[51] Int. Cl.[6] .................................................. G01N 11/12
[52] U.S. Cl. .................. 436/69; 436/174; 436/180; 436/43; 422/73; 422/81; 422/100; 73/54.15; 73/54.18
[58] Field of Search ........................ 422/73, 68.1, 81, 422/100, 102; 436/69, 174, 179, 180, 43; 73/54.15, 54.18

[56] References Cited

U.S. PATENT DOCUMENTS

| Re. 27,866 | 1/1974 | Adler | 23/253 R |
|---|---|---|---|
| 3,635,678 | 1/1972 | Seitz et al. | 23/230 R |
| 3,836,333 | 9/1974 | Mintz | 23/259 |
| 3,967,934 | 7/1976 | Seitz et al. | 23/253 R |
| 4,276,383 | 6/1981 | Leighton et al. | 435/291 |
| 4,388,823 | 6/1983 | Garnaud et al. | 73/57 |
| 4,599,219 | 7/1986 | Cooper et al. | 422/61 |
| 4,648,262 | 3/1987 | Reis et al. | 73/57 |
| 4,725,554 | 2/1988 | Schildknecht | 436/69 |
| 4,752,449 | 6/1988 | Jackson et al. | 422/73 |
| 4,852,388 | 8/1989 | Park et al. | 73/32 R |
| 4,876,069 | 10/1989 | Jochimsen | 422/73 |
| 4,879,432 | 11/1989 | Viellard | 436/69 |
| 5,072,610 | 12/1991 | Martinoli et al. | 73/64.1 |
| 5,154,082 | 10/1992 | Mintz | 73/64.41 |
| 5,260,872 | 11/1993 | Copeland et al. | 364/413.07 |
| 5,300,779 | 4/1994 | Hillman et al. | 250/341 |
| 5,302,348 | 4/1994 | Cusack et al. | 422/73 |
| 5,372,946 | 12/1994 | Cusak et al. | 436/69 |

*Primary Examiner*—Long V. Le
*Attorney, Agent, or Firm*—Dorr, Carson, Sloan & Birney, P.C.

[57] ABSTRACT

An apparatus for detecting changes in the viscosity of a fluid comprises a cartridge having a fluid receiving/dispensing reservoir, one or more fluid-receiving chambers, and a conduit that permits fluid communication between the fluid receiving/dispensing reservoir and the fluid-receiving chamber. Fluid is introduced into the cartridge through an injection port and fills the reservoir, moving from the reservoir through the conduit into the chamber. An air vent/fluid plug device in fluid communication with the chamber permits air to exit while the fluid enters the system but prevents the fluid from leaving after the chamber is filled. A freely movable ferromagnetic material is placed within the fluid-receiving chamber and is caused to move by an electromagnet. Changes in the viscosity of the fluid are detected by determining the position of the ferromagnetic material in the fluid-receiving chamber.

31 Claims, 9 Drawing Sheets

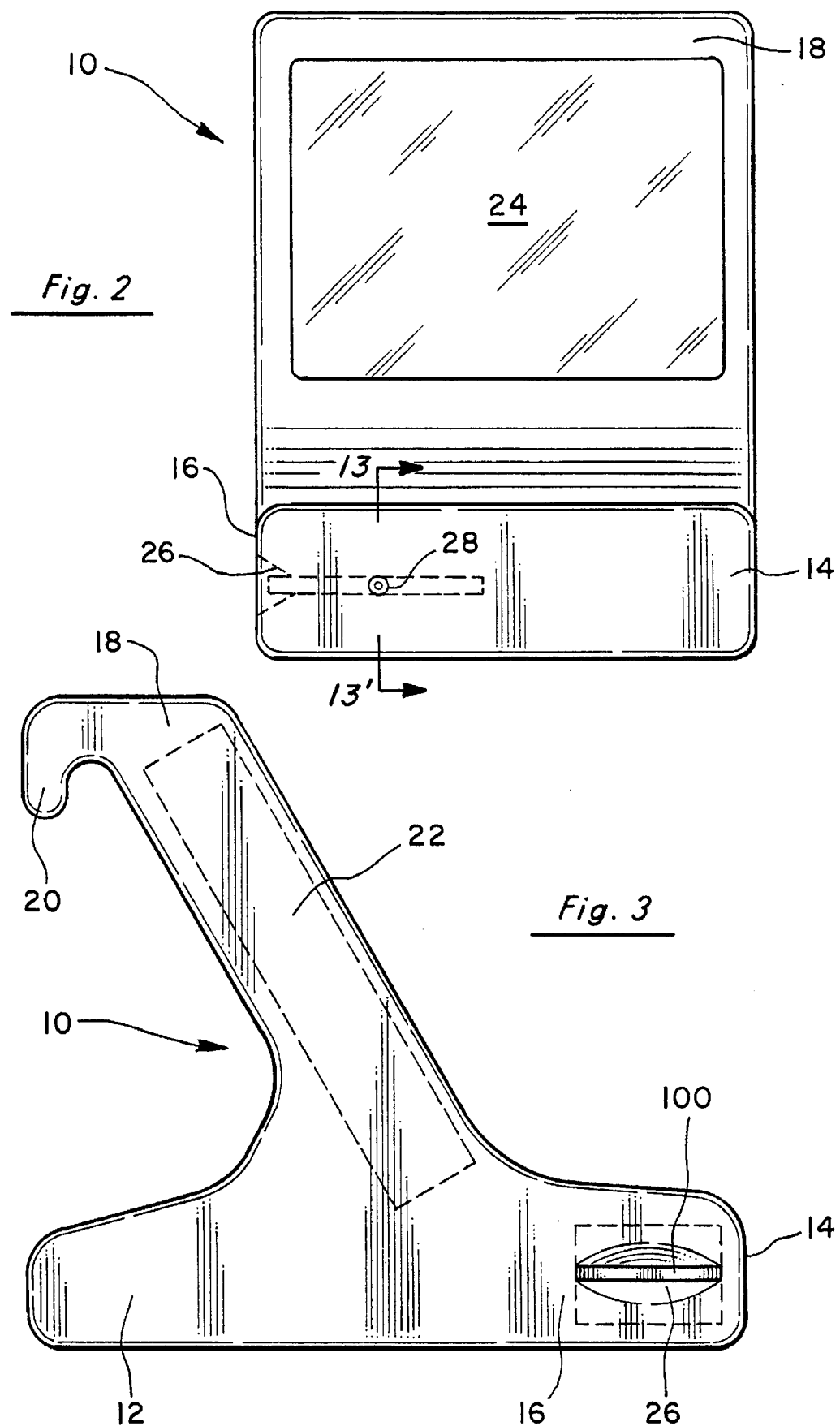

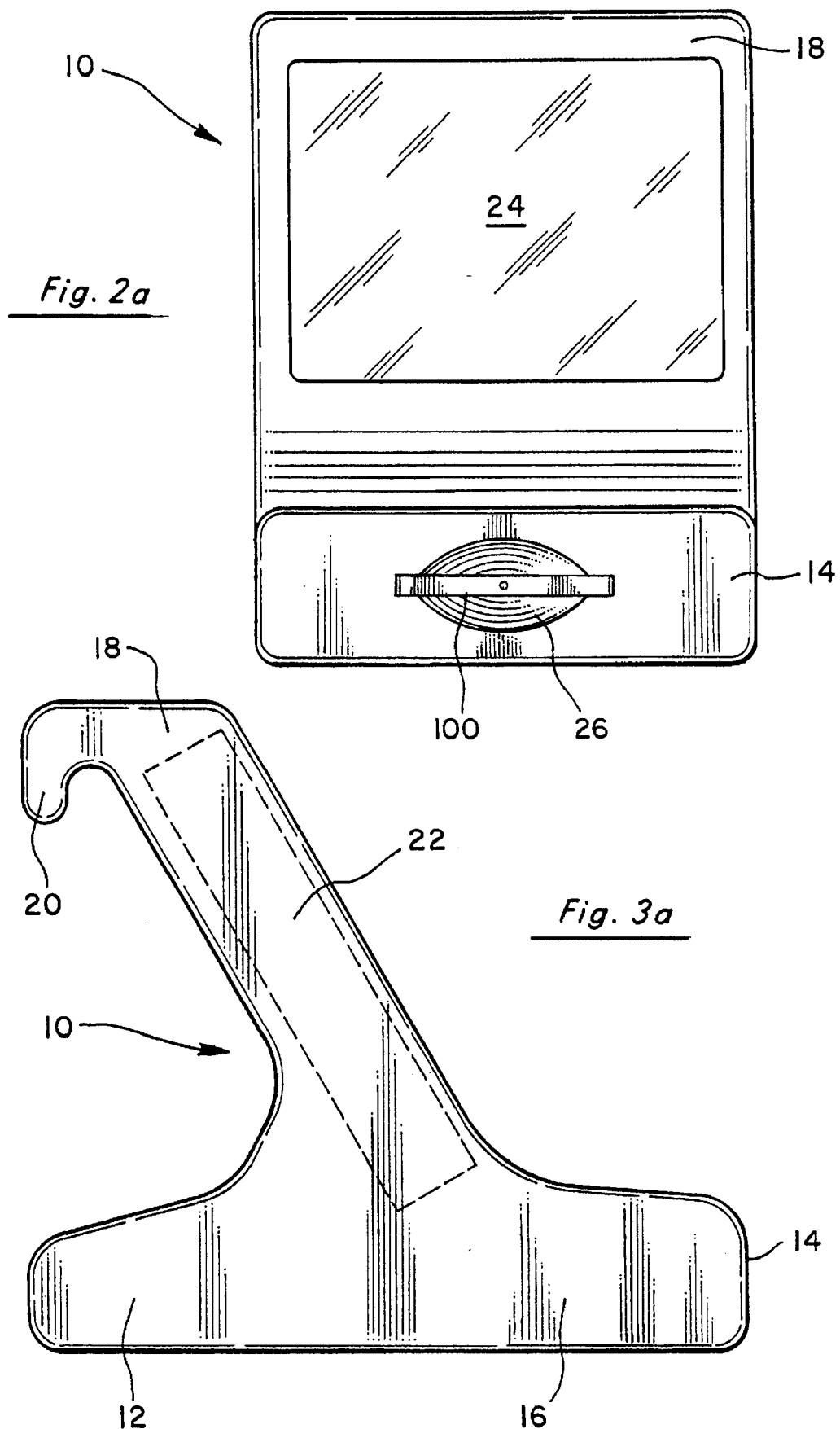

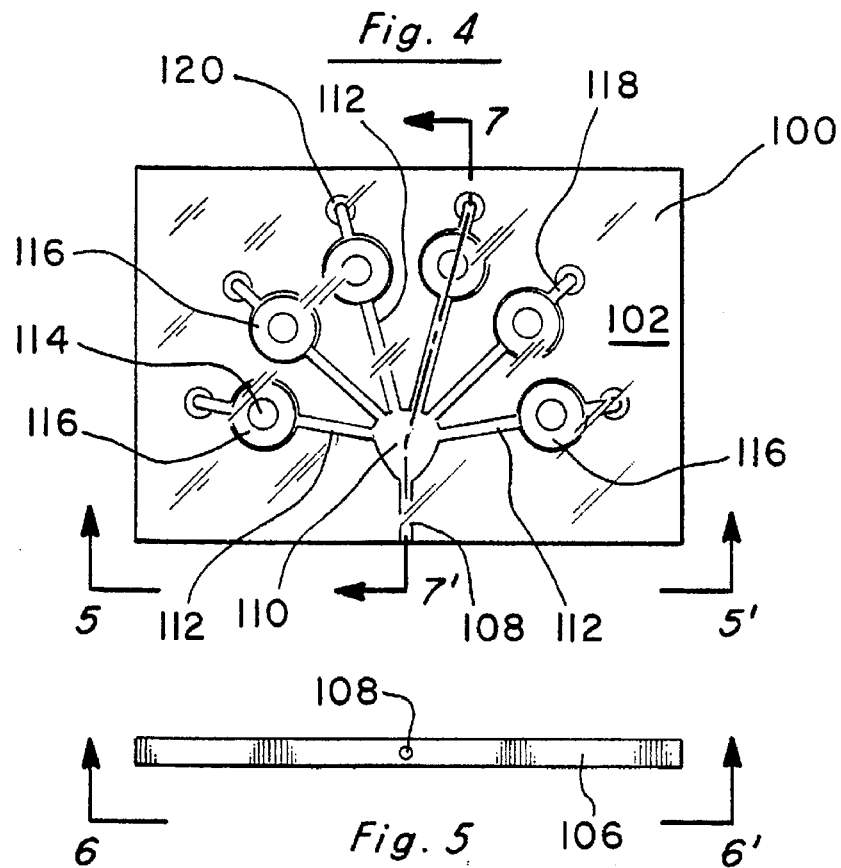
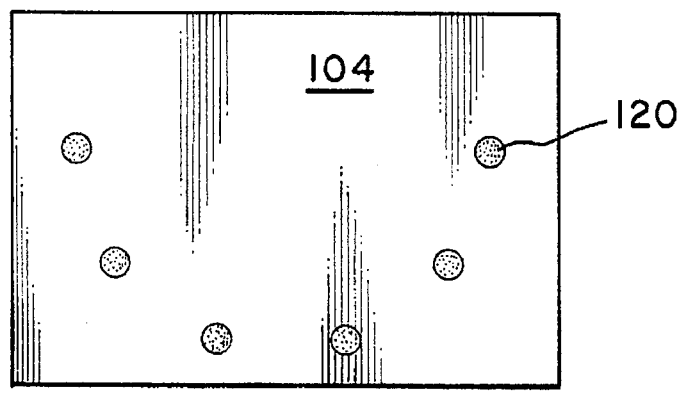
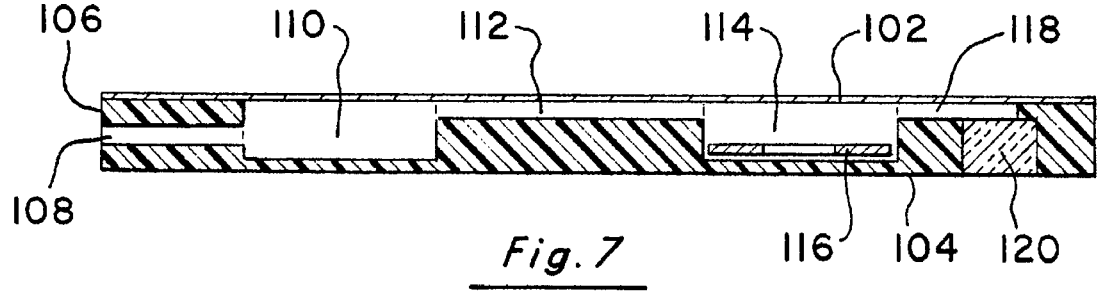

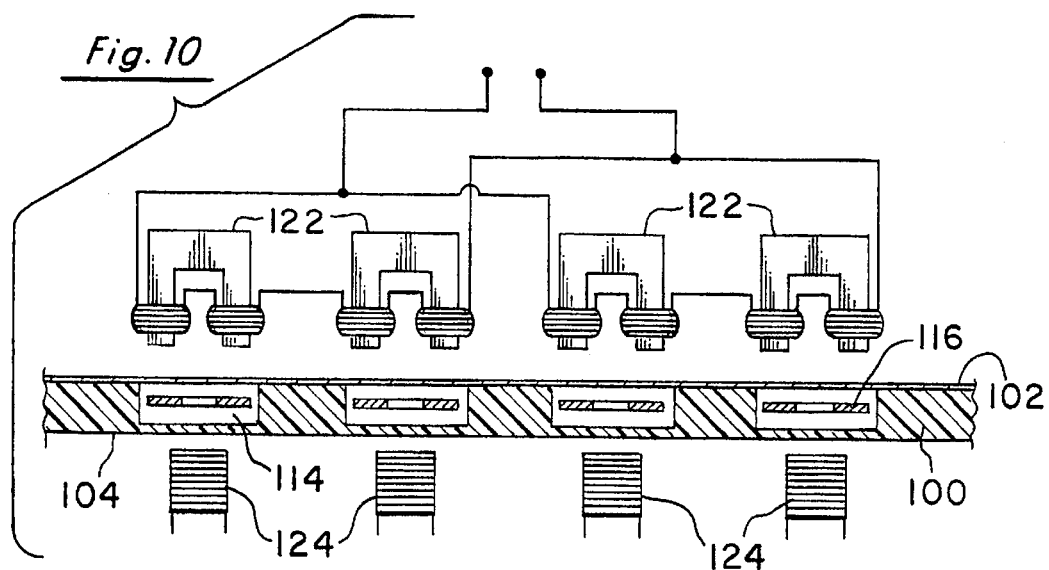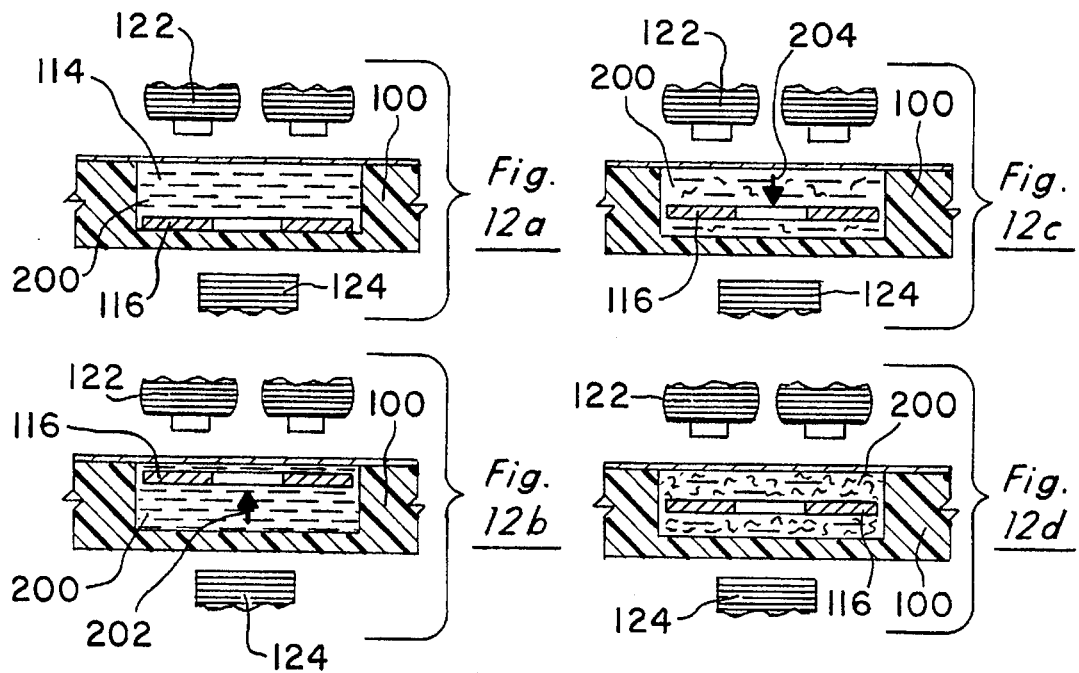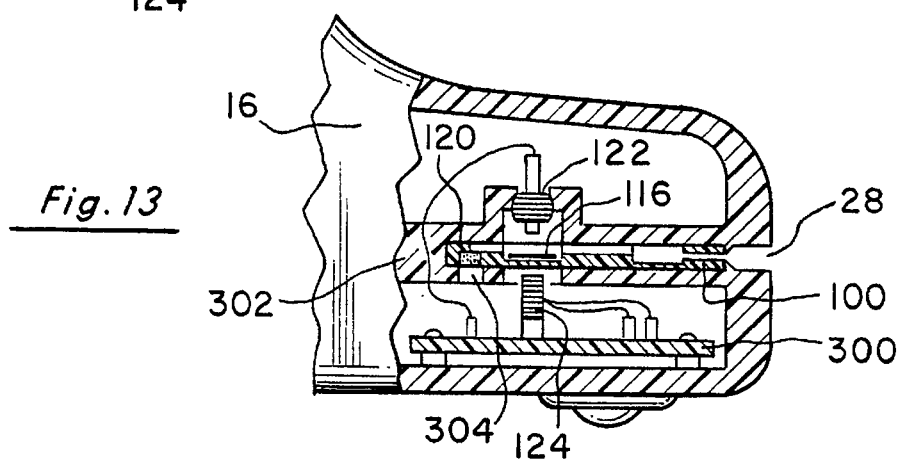

METHOD AND APPARATUS FOR DETECTING VISCOSITY CHANGES IN FLUIDS

BACKGROUND OF THE INVENTION

1. Field of the Invention

The present invention relates in general to detection of changes in viscosity of a fluid and, more particularly, to detection of changes in viscosity of blood that has been treated with viscosity-altering substances.

2. Statement of the Problem

The ability to detect changes in viscosity of fluids such as blood, food products, and various other liquid compositions (e.g., industrial fluids, oil production fluids, etc.) can have immense practical value. For example, the ability to detect changes in viscosity of human blood resulting from blood coagulation can have tremendous consequences since the balance between normal hemostasis and coagulation or anticoagulation is essential in maintaining the integrity of the circulatory system and in stopping both external and internal bleeding. However, it is sometimes necessary to modify the natural coagulation system, either by increasing or by decreasing the rate of blood coagulation. For example, during open heart surgery, a patient must often be supported by a heart/lung bypass machine that provides extracorporeal blood circulation while the heart is stopped. To prevent blood from clotting upon exposure to the bypass apparatus, the patient is treated with high doses of heparin, a naturally occurring substance that significantly prolongs the clotting time of blood. When the time comes to remove the patient from the heart/lung bypass machine, however, it is desirable for the patient's blood to regain its normal coagulation characteristics so that it will again be able to clot and assist in healing incisions and stopping internal or external bleeding. This reversal of the effects of heparin is achieved by treating the patient's blood with an anticoagulant-reversing substance, such as protamine, capable of neutralizing heparin or other anticoagulating substances.

To successfully maintain anticoagulation during a surgical procedure and neutralize the heparin at the conclusion of surgery, it is necessary to determine the concentration of heparin in the patient's blood. It is extremely important during surgery that this determination be made quickly and accurately using a minimal blood sample. Since the activity of heparin varies from batch to batch and patient to patient, this determination cannot be made on the basis of the amount of heparin administered. Protamine also varies in potency from batch to batch and from patient to patient. Allergic responses to protamine also have been reported. Furthermore, protamine itself acts as an anticoagulant. Thus, for optimal reversal of heparin action, it is essential to use only that amount of protamine that will directly neutralize the amount of active heparin in the blood being circulated.

In addition to preventing coagulation of blood during heart/lung bypass surgery, it is often desirable to lower the tendency of blood to coagulate on a long-term basis. Long-term anticoagulant treatment has applications for preventing strokes, pulmonary embolisms, and thromboses, for hemodialysis, and for treatment after acute myocardial infarction. Such long-term treatments do however require lower dosages of anticoagulant compared to those used during surgical procedures. Long-term treatments also require the clotting time of blood to be confined within a narrower range.

In view of the varying activities of anticoagulants such as heparin and the varying responses of patients to anticoagulants, it is essential to monitor anticoagulant therapy closely. Dose-response tests measure changes in clotting time in response to differing doses of anticoagulant in order to determine the correct dose of anticoagulant for a particular patient. Clotting time or activated clotting time tests are used to determine whether the blood has achieved the desired level of anticoagulation. Heparin/protamine (anticoagulant/neutralizer) titrations provide a quantitative determination of heparin (anticoagulant) levels. Such tests are based on measuring the time necessary for the blood to coagulate.

Many methods have been developed to measure changes in the viscosity of fluids, including measuring the coagulation time of blood as an empirical measure of blood viscosity. Manual methods for accomplishing clotting time tests are well known to this art. However, these manual methods require relatively long times and large fluid samples and are subject to variable results and inaccuracies due to operator variances. As a result, it is desirable to provide methods and apparatus to automate these tests in order to provide quick, consistently accurate analytical tests. The following patents describe a variety of such apparatus and methods.

U.S. Pat. Nos. 3,635,678 and 3,967,934 to Seitz et at. describe an apparatus for determining changes in viscosity of a fluid held within a test tube. A steel ball is held at a certain location in the test tube by a magnet while the tube moves up and down. When the fluid in the tube clots, the steel ball changes position relative to the magnet, and this change in position is detected photoelectrically.

U.S. Pat. No. Re. 27,866 to Adler depicts an apparatus in which the coagulation of a blood plasma sample is intensified by dispersing iron oxide particles throughout the sample and then subjecting the particle-sample mixture to a rotating magnetic field that causes the particles to move within the sample and activate the clotting reaction. When the fluid produces fibrin strands, the moving particles collect these strands, changing the optical properties of the particle-sample mixture. The change in optical properties is detected by light-sensitive means.

U.S. Pat. Nos. 3,836,333 and 5,145,082 to Mintz describe a blood coagulation detection apparatus in which a blood sample is placed in a test tube with a ferromagnetic member. The test tube is then rotated about its axis, producing a relative motion between the tube and the ferromagnetic member; that is, as the tube rotates, the ferromagnetic member remains in the same predetermined position within the tube. When the blood in the tube clots, the ferromagnetic member is displaced from this predetermined position, and movement of the member is sensed magnetically with a reed switch.

Cooper et al. (U.S. Pat. No. 4,599,219) and Jackson et at. (U.S. Pat. No. 4,752,449) each describe an apparatus and method in which a plunger assembly is repeatedly raised and released so that it descends through a sample of fluid contained within a tubular cartridge. The cartridge includes an upper chamber in which the fluid sample is injected via syringe and a lower chamber containing any desired viscosity-altering substances, and means to seal the upper chamber and communicate the contents of the lower chamber to the upper chamber. The plunger is raised mechanically, and its position is sensed by an optical detector. When the viscosity of the fluid sample increases, the plunger will descend more slowly through the fluid sample.

U.S. Pat. No. 4,648,262 to Reis et al. describes a viscometer in which the fluid sample whose viscosity is to be measured is placed in a capillary tube along with a metal ball. A magnet mounted on a rotating drum periodically raises the ball to the top of the tube and then releases the ball to fall to the bottom of the tube. The viscosity of the fluid is determined by the rate of descent of the ball in the tube.

U.S. Pat. No. 4,879,432 to Vieillard provides a method and apparatus to measure coagulation of blood in which a stream of solid particles is established in a tube containing the blood and the time at which the stream of particles is stopped marks the coagulation of the blood. The particles are micron-sized grains of, for example, glass, that are highly wettable so that they travel down the tube under the effect of gravity. Their small size means that they are immediately stopped by the fibrin network as soon as coagulation has begun. Photoelectric cells detect the stopping of the particles.

U.S. Pat. Nos. 5,302,348 and 5,372,946 to Cusack et at. describe a cuvette used for performing a coagulation time test on blood. The blood is deposited into a fluid reservoir on a disposable cuvette. The blood is then drawn by a machine from the reservoir into a capillary conduit within the cuvette. The capillary conduit has a narrower region at one point along its length. The machine causes the blood in the conduit to move back and forth, traversing the narrow region. The time the blood requires to traverse the narrow region of the conduit is measured during each iteration. When this traversal time increases by a predetermined amount over the immediately preceding time, the blood is considered to have coagulated.

Various problems and drawbacks exist with these previous methods and apparatus for automating fluid viscosity determinations. Some of these problems are particularly noteworthy in the realm of surgery. For example, nearly all the methods described above require large samples that are manually obtained and manually metered into the apparatus, thereby exposing the operator to contact with the blood as well as introducing operator error and/or inconsistencies when measuring the volume of the test sample. Moreover, most of these methods allow only one test chamber to be measured at a time. In effect, this one test chamber approach prevents analyses, such as heparin/protamine titration, that require simultaneous testing in multiple chambers. The previous methods and apparatus also are limited in allowing only one type of test to be run per chamber or cartridge, and many have a very limited test menu. It should also be noted that many of these prior art apparatus are complicated to use and are not readily adaptable to use in a surgical environment. Moreover, the test results from many of these prior art apparatus do not reliably relate to the test results available from recognized and accepted, albeit slow, manual analytical laboratory techniques. Hence, many physicians do not consider such automated devices to be reliable.

It would therefore be desirable to have the ability to conduct multiple viscosity-related analytical tests quickly, reliably, and reproducibly during surgical and clinical procedures. It would also be desirable if such tests could be carried out by an automated apparatus that is easy to use and not subject to variability introduced by operator inconsistencies. It also is highly desirable that the disposable elements of an apparatus used to carry out such tests be self-contained, inexpensive, and capable of withstanding reasonable storage periods under a variety of conditions.

SUMMARY OF THE INVENTION

The apparatus of the present invention is able to detect changes in the viscosity of a fluid sample quickly, accurately, and repeatably. Each disposable cartridge of the apparatus of the present invention is capable of containing a large and variable number of test chambers, allowing several types of viscosity-related tests to be performed simultaneously using a single cartridge. Each type of analytical test is performed quickly, accurately, and reliably. The volume of the fluid samples used is minimal and the amount of fluid contained within each test chamber is automatically determined and thus varies little from test to test. Thus, discrepancies that may be introduced by individual procedures of technicians are eliminated. The disposable cartridges of the present invention are inexpensive to manufacture and small in size, thereby reducing the amount of storage space needed. Any viscosity-altering substances such as protamine placed within the cartridges may be, and preferably are, dried so that storage life is extended, even under less-than-ideal storage conditions. Moreover, because the operation of the herein-described apparatus is completely automatic, it is extremely simple to use and operator-caused errors and/or inconsistencies are virtually eliminated.

The present invention is particularly well suited for clotting time tests, dose-response tests, and titration tests on human blood and especially for tests on blood from patients undergoing anticoagulation therapy during heart/lung bypass surgery wherein the effects of the large amounts of heparin needed to prevent clotting of their blood must be closely monitored. The methods and apparatus of the present invention are also sensitive enough to perform tests on blood samples from patients who receive only small amounts of anticoagulants on a long-term basis to reduce the risk of stroke or other embolisms and thromboses.

The test procedures of this patent disclosure commence when a fluid sample to be tested is introduced through an injection port, either manually or automatically, into a fluid receiving/dispensing reservoir contained within applicants' disposable cartridge. From the fluid receiving/dispensing reservoir the fluid moves through a conduit leading to a fluid-receiving chamber. More preferably, the fluid receiving/dispensing reservoir is provided with two or more (and most preferably from two to six) separate conduits that each lead to a respective fluid-receiving chamber. Such a reservoir-conduit-chamber fluid communication system enables all the chambers to be filled simultaneously. Each fluid-receiving chamber is provided with an air vent/fluid plug device that is in fluid communication with its associated fluid-receiving chamber. Air contained within the reservoir, conduit(s), and chamber(s) is vented through this air vent/fluid plug device(s) as fluid enters the system. The air vent/fluid plug device, although porous to air, is non-porous to fluid; thus, when fluid reaches the air vent/fluid plug device, the air vent/fluid plug device establishes a fluid lock and thereby prevents any further movement of fluid within the cartridge.

At least one, and preferably each, fluid-receiving chamber also contains a freely movable ferromagnetic material. When a viscosity analysis is performed, the ferromagnetic material is raised to the top of the chamber and then is permitted to fall through the fluid to the bottom of the chamber. The time of descent is measured by detecting the position of the ferromagnetic material. This reciprocating motion of the ferromagnetic material is repeated until a change in fall time in one or more chambers signals a change in the viscosity of the fluid within those one or more chambers.

A viscosity-altering substance may be, and preferably is, included in the apparatus of the present invention. For example, viscosity-altering substances can be placed at any desired location within the cartridge (e.g., in the injection port, in the fluid receiving/dispensing reservoir, in one or more conduits, in one or more fluid-receiving chambers, or in combinations thereof). In the case of a heparin/protamine titration test, for example, a different amount of protamine, which is a heparin neutralizer, can be placed within each of one or more conduits or one or more fluid-receiving chambers or combinations thereof before a heparinized blood sample is introduced into the cartridge. The blood mixes with the protamine as it travels through the reservoir-conduit-chamber system. After the blood fills the chambers, the apparatus proceeds to raise the ferromagnetic material in one or more of the chambers and measure the fall time of that ferromagnetic material. Useful inferences are then made from such fall times (relative to some standard and/or relative to fall times in different chambers within the system; for example, the chamber in which the blood clots first is the chamber in which the protamine level is closest to the heparin level of the blood sample).

Expressed in patent claim language, such an apparatus for detecting changes in viscosity of a fluid would comprise: (1) a cartridge having a fluid receiving/dispensing reservoir, one or more fluid-receiving chambers, and a conduit that permits fluid communication between the fluid receiving/dispensing reservoir and the fluid-receiving chamber; (2) an injection port in the cartridge for introducing fluid into the fluid receiving/dispensing reservoir; (3) an air vent/fluid plug device in fluid communication with the fluid-receiving chamber; (4) a ferromagnetic material that is free to move in the fluid-receiving chamber; (5) means for moving the ferromagnetic material in the fluid-receiving chamber; and (6) means for detecting the position of the ferromagnetic material in the fluid-receiving chamber. Optionally, the cartridge may be provided (at various places) with one or more viscosity-altering substances in equal or varying amounts.

Thus, one of the main objects of the present invention is to provide an apparatus and method to measure, quickly, accurately, and reliably, changes in the viscosity of a fluid.

It is another object of the present invention to provide an apparatus that is fully automated in operation to reduce the occurrence of operator-induced errors and inconsistencies, is simple to use, is inexpensive to manufacture, and is capable of being stored for long periods of time in a small amount of space.

It is an additional object of the present invention to provide an apparatus capable of performing more than one type of viscosity-related analysis at one time using a minimal volume of fluid sample for each test.

It is yet another object of the present invention to provide a method by which the multiple test chambers of the cartridge are automatically simultaneously and completely filled.

It is a further specific object of the present invention to provide an apparatus and method to determine changes in the coagulation state of human blood treated with high doses of anticoagulants.

Another specific object of the present invention is to provide an apparatus and method to monitor the coagulation state of human blood from patients treated over long periods with low doses of anticoagulants.

These and other advantages, features, and objects of the present invention will be more readily understood in view of the following detailed description and the drawings.

BRIEF DESCRIPTION OF THE DRAWING

The present invention can be more readily understood by reference to the accompanying drawings, in which:

FIGS. 2 and 2a are from elevational views of the machine of the present invention.

FIGS. 3 and 3a are side elevational views of the machine of the present invention.

FIG. 4 is a top plan view of the cartridge of the present invention.

FIG. 5 is a front elevational view of the cartridge.

FIG. 6 is a bottom plan view of the cartridge.

FIG. 7 is a cross-sectional view of the cartridge of the present invention, shown substantially along section line 7—7' of FIG. 4.

FIG. 8c is a cut-away, side view of the ferromagnetic disk as shown along section line 8—8' of FIG. 8a.

FIG. 10 is a partial cross-sectional view of the cartridge of the present invention showing certain relationships between a plurality of ferromagnetic disks in a cartridge and an array of electromagnets and position detection devices.

FIG. 11b is a continuation of the test procedure depicted in FIG. 11a.

FIGS. 12a–12d are sequential partial cross-sectional views of a chamber of the present invention illustrating the motion of the ferromagnetic material in the chamber.

FIG. 13 is a cross-sectional view of the cartridge shown positioned within the machine of the present invention, shown substantially along section line 13—13' of FIG. 2, with the section through the cartridge shown substantially along section line 7—7' of FIG. 4.

DETAILED DESCRIPTION OF PREFERRED EMBODIMENTS

1. Test Procedures

Figure 1:
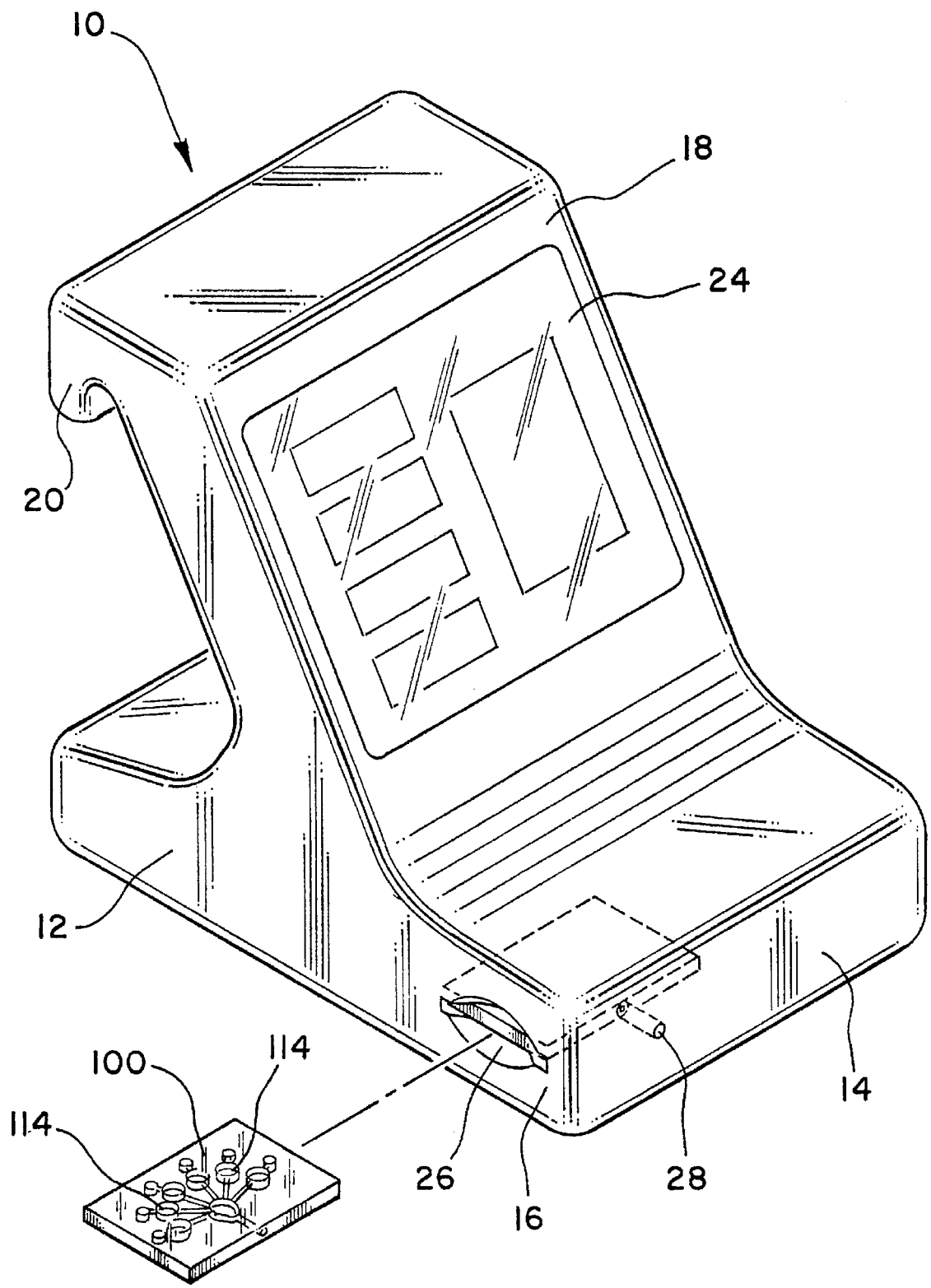
FIGS. 1 and 1a are perspective views of a cartridge and a machine with which the cartridge is used in accordance with the teachings of the present invention.
Figure 1A:
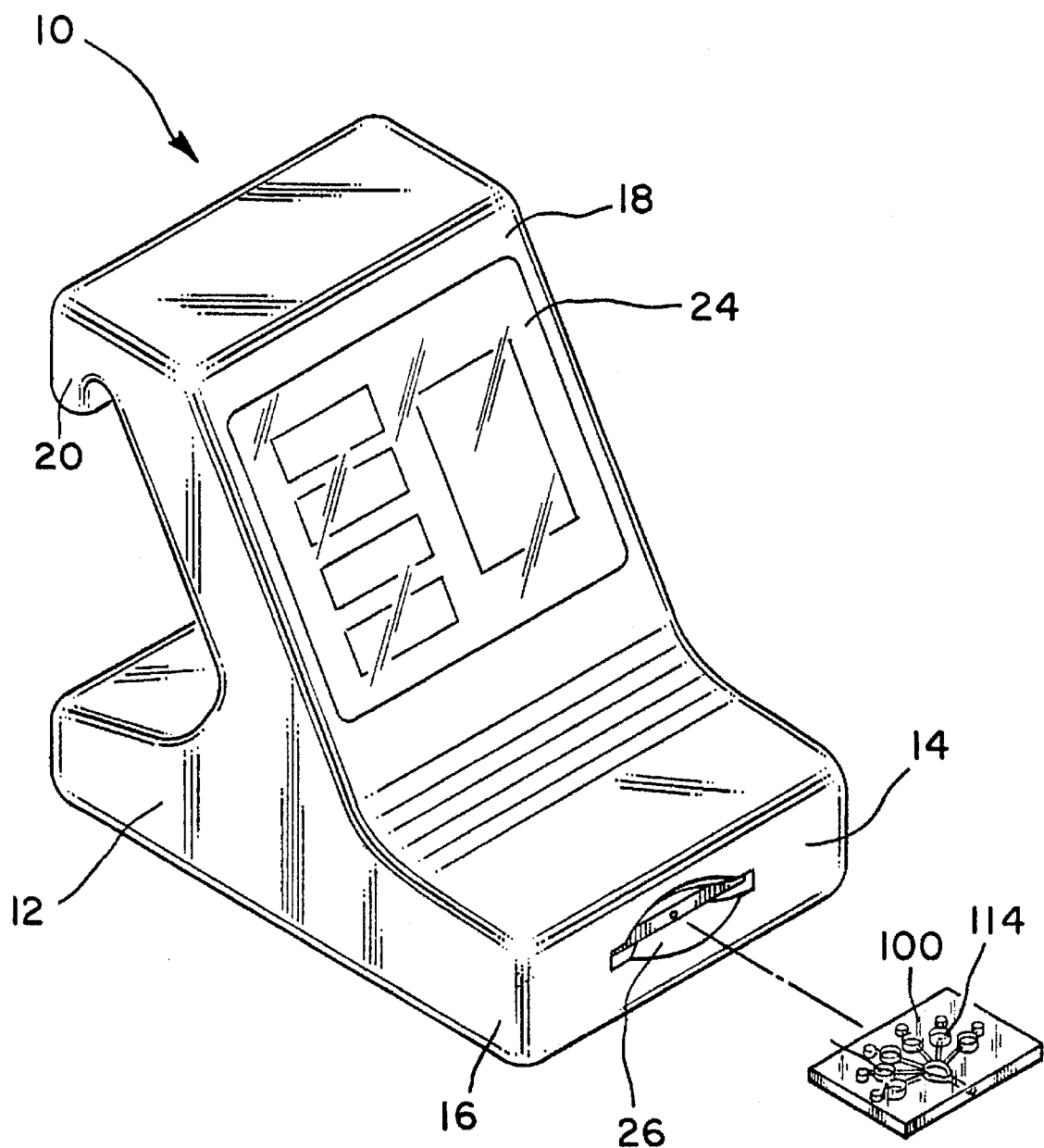

FIG. 1 depicts a disposable cartridge 100 associated with a fluid viscosity testing device 10 (hereinafter called a "machine" 10) according to the teachings of this patent disclosure. The cartridge 100 and machine 10 comprise apparatus for detecting the viscosity of a fluid, measuring the elapsed time required for the viscosity to change, and deriving and displaying that (and other information) concerning the fluid. If the fluid is blood, information concerning the patient may also be displayed. In operation, the cartridge 100 may be inserted into the machine 10 before or after the cartridge is filled with the fluid whose viscosity is to be tested. Most preferably, the cartridge 100 includes a plurality of fluid-receiving chambers 114. The machine 10 then conducts an analytical test following a predetermined procedure in accordance with the type of analysis desired. By use of the cartridge 100, the machine 10 accurately, reliably, and quickly conducts various tests, including, but not limited to, viscosity-related tests, for example, blood coagulation time tests, dose-response tests, and titration tests. FIGS. 2 and 3, respectively, show the machine 10 in front and side elevational views. FIGS. 1a, 2a, and 3a illustrate an alternative embodiment in which the cartridge 100 is inserted into the front of the machine 10.

After a cartridge 100 containing a fluid sample is placed in the machine 10, a ferromagnetic material such as the ferromagnetic washer 116 shown in FIGS. 4 and 7 residing within a given fluid-receiving chamber 114 is raised through the fluid sample and allowed to drop. The machine 10 then detects and measures the time required for the ferromagnetic material 116 to fall through the fluid sample. As the viscosity of the fluid changes (either increasing or decreasing), the fall time of the ferromagnetic material 116 through the fluid sample will change correspondingly. The machine 10 is further able to distinguish the type of analytical test to be conducted and to compute the results of the test based on this determination. These test results may then be compared (for example, through computer-programmed comparisons) with other programmed test information and/or with other test results.

The apparatus and test methods of the present invention can be further appreciated from the following.

2. Cartridge 100

Figure 9:
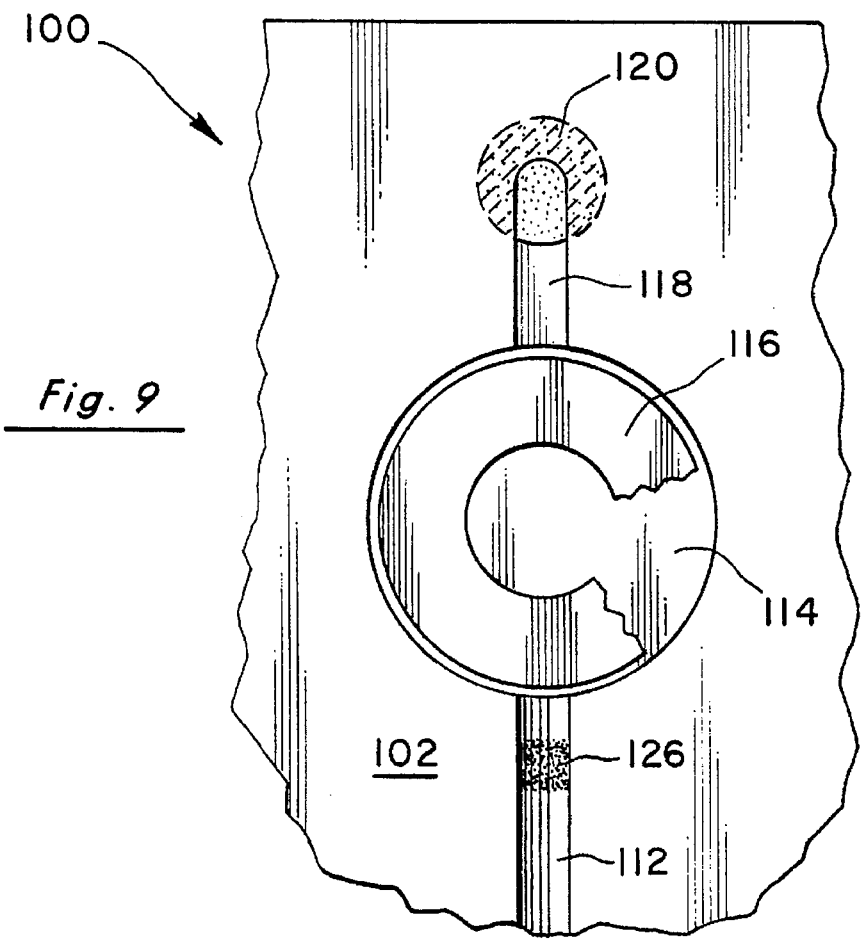
FIG. 9 is an enlarged partial cut-away top plan view of the conduit, fluid-receiving chamber provided with a ferromagnetic disk, and air vent/fluid plug device of the cartridge of the present invention.

A cartridge 100 is shown in greater detail in FIGS. 4 through 7 as well as FIG. 9. A top view of a preferred embodiment of the cartridge 100 is shown in FIG. 4. The cartridge 100 is substantially planar and formed of a rigid substantially integral material, for example, a plastic or acrylic, that is, most preferably, inert with respect to the fluid sample being tested. The rigid material from which the cartridge 100 is formed may be partially or wholly transparent. The cartridge 100 may be manufactured as a unitary or monolithic piece (for example, by injection molding techniques), or the cartridge 100 may be assembled from various separate parts. In one particularly preferred embodiment, a separate and distinct top 102 is attached to the cartridge 100 after a viscosity-altering substance is placed in the cartridge 100, as explained in greater detail in later sections of this patent disclosure. In one particularly preferred embodiment of this invention, the top 102 is a stiff, transparent, plastic material such as Mylar®; however, it is to be understood that various types of materials may be used for such tops 102 so long as they provide a fluid-impervious seal between the top 102 and the cartridge 100.

As shown in FIG. 5, an injection port 108 is preferably provided in a nominal front portion 106 of the cartridge 100 for admission of the fluid sample into the cartridge 100. The injection port 108 directs the fluid sample into a fluid receiving/dispensing reservoir 110. From the fluid receiving/dispensing reservoir 110 the fluid proceeds through one or more conduits 112 to each conduit's respective fluid-receiving chamber 114. The motive force for this movement of the fluid through the cartridge 100 is provided by a fluid injection or pumping mechanism, for example, a manually activated syringe, or by other methods, such as by suction, for example, a vacuum system. Most preferably, each fluid-receiving chamber 114 is equidistant from the fluid receiving/dispensing reservoir 110, so that the fluid moves from the fluid receiving/dispensing reservoir 110 simultaneously or nearly so into each fluid-receiving chamber 114. In those embodiments of this invention in which the fluid being tested is human blood, each fluid-receiving chamber 114 will preferably have a volume of about 100 µl to about 250 µl. Although six fluid-receiving chambers 114 are shown in FIG. 4, it should be understood that any desired number of fluid-receiving chambers 114 in any desired orientation can be formed in the cartridge 100 and that the scope of the present invention encompasses other orientations, configurations, numbers, and sizes of any such fluid-receiving chamber 114.

Again, in the most preferred embodiments of this invention, multiple fluid-receiving chambers 114 should be filled nearly simultaneously to ensure accuracy of the analytical test results. To achieve this near-simultaneous filling, the fluid receiving/dispensing reservoir 110 is preferably provided with a substantially triangular configuration so that it acts as a uniform manifold to deliver the fluid to the fluid-receiving chambers 114. The injection port 108 is in fluid communication with the fluid receiving/dispensing reservoir 110. As seen in FIG. 7, the injection port 108 is most preferably equidistant from the top 102 and the bottom 104 of the cartridge 100 and relatively closer to the bottom of the fluid receiving/dispensing reservoir 110. The conduits 112 preferably are arrayed along the fluid receiving/dispensing reservoir 110 opposite from the region where the injection port 108 enters the fluid receiving/dispensing reservoir 110, and the conduits 112 most preferably are located closer to the top of the fluid receiving/dispensing reservoir 110 relative to location of the injection port 108. Thus, the fluid sample enters one end of the fluid receiving/dispensing reservoir 110 via the injection port 108 and substantially fills the fluid receiving/dispensing reservoir 110 before reaching the conduits 112 at the opposing end of the reservoir 110.

Any air contained in the cartridge 100 must be vented from the cartridge 100 as the fluid sample enters. To this end, a second conduit 118 leads from the fluid-receiving chamber 114 to an air vent/fluid plug device 120 such as the one shown in FIG. 9. As the fluid sample enters the cartridge 100 and moves into any given fluid-receiving chamber 114, air contained in the fluid receiving/dispensing reservoir 110, first conduit 112, and fluid-receiving chamber 114 is vented through the second conduit 118 and out of the cartridge 100. For example, most preferably this venting can be done through the bottom 104 of the cartridge 100 (as seen in FIG. 6) through the air vent/fluid plug device 120. This venting can be done through the top or sides of the cartridge 100 as well. The second conduit 118 preferably exits the chamber 114 at a position that is substantially opposite the position where the first conduit 112 enters the chamber 114 and, as seen in FIG. 7, at the same level with respect to the top of the fluid-receiving chamber 114. This arrangement permits the fluid sample to fill a given chamber 114 before it reaches the second conduit 118 and exits the chamber 114. In the alternative, this second conduit 118 can be an integral part of the air vent/fluid plug device 120. In either case, when fluid reaches the air vent/fluid plug device 120, a permanent fluid lock forms that prevents any further motion of fluid through that fluid-receiving chamber 114. The air vent/fluid plug device 120 therefore allows air displaced by incoming fluid to exit the cartridge 100, but prevents fluid from leaving the cartridge 100 via the air vent/fluid plug device 120. In one of the more preferred embodiments of this invention, the air vent/fluid plug device 120 is formed of Porex® plastic (Porex Corp. no. X6870). This material is porous to a gas such as air, but is not porous to a liquid such as blood, and therefore acts as a fluid lock. The fluid communication system created by the fluid receiving/dispensing reservoir 110, conduit(s) 112 (and 118), fluid-receiving chamber(s) 114, and air vent/fluid plug device(s) 120 automatically enables the correct amount of fluid to fill each fluid-receiving chamber 114, so that no measurements need to be made by human operators. This automatic measuring action provides a means whereby the volume of the fluid samples will not vary between the respective chambers 114, or between tests. Fail-safe provisions also may be provided by the machine 10 to disclose incomplete filling of the fluid-receiving chambers 114.

Figure 8A:
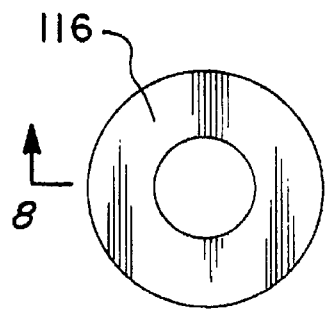
FIG. 8a is an enlarged top plan view of a ferromagnetic disk of the present invention.
Figure 8B:
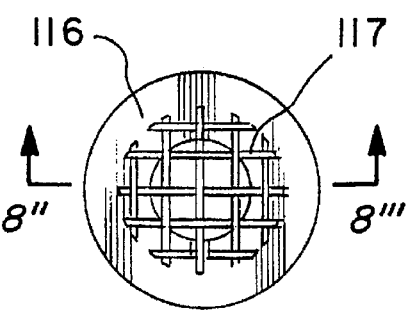
FIG. 8b is an enlarged top plan view of a ferromagnetic disk of the present invention provided with an attached screen.
Figure 8C:
Figure 8D:
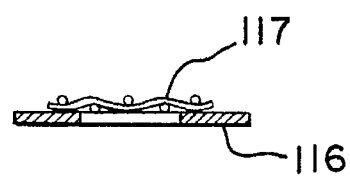
FIG. 8d is a cut-away, side view of the ferromagnetic disk with screen as shown along section line 8"—8"' of FIG. 8b.

Within at least one, but preferably within each of several fluid-receiving chambers 114 is placed a ferromagnetic material 116 such as iron, nickel, cobalt, and numerous alloys known to the art. Such a ferromagnetic material may act both to induce and to measure viscosity changes in the fluid. In one preferred embodiment, this ferromagnetic material 116 is a single piece such as a washer made of steel or other iron-based alloy. Such a washer-like configuration is depicted in FIGS. 8a and 8c. It is important in order to ensure accurate and reliable results of the analytical tests that each washer 116 employed meet strict specifications, especially as to its physical measurements. Although the ferromagnetic material 116 used in the preferred embodiment will normally be a steel or other iron-based alloy washer, it should be understood that other magnetically affected materials and other shapes are within the scope of the present invention. Hence, references herein to "washers" may include other materials and shapes. By way of example only, the ferromagnetic material 116 can be formed into beads, large particles, or even filings. A second embodiment of the ferromagnetic washer 116 is illustrated in FIGS. 8b and 8d. In this embodiment, a screen 117 is brazed to the top of the washer 116. The advantages of the screen 117 are discussed below. The essential attribute is that the ferromagnetic material 116 be freely movable in the fluid within the fluid-receiving chamber 114. Such ferromagnetic material can be moved under the action of a magnet or by other means, for example, by the force of gravity. In any case, the ferromagnetic material 116 most preferably will not have a large volume relative to the volume of the fluid-receiving chamber 114. In the context of blood testing, applicants have found that if a washer 116 is employed it should preferably displace a volume of about 10 μl to about 50 μl. Thus, the volume of fluid sample that can be injected into a given fluid-receiving chamber 114 is preferably about 50 μl, to about 240 μl, based on a total chamber 114 volume of about 100 μl to about 250 μl.

Viscosity-altering substances 126 may be added to the fluid sample before or after the fluid is introduced into the cartridge 100. Most preferably, one or more types of viscosity-altering substances 126 are placed at one or more locations within the cartridge 100. One particularly preferred position for a viscosity-altering substance 126 is at the output end of the first conduit 112 nearest the fluid-receiving chamber 114, as shown in FIG. 9. So positioned, the fluid sample will be thoroughly mixed with the viscosity-altering substance 126 as the fluid enters the chamber 114. However, the viscosity-altering substance 126 may be placed anywhere in the cartridge 100 where it will contact the fluid sample, but preferably before the fluid reaches the second conduit 118, and, most preferably, where the location permits thorough mixing of the viscosity-altering substance 126 with the fluid.

When the viscosity-altering substance 126 is made a part of the cartridge 100 it is preferably in a dried form to prevent loss of its activity during storage. In an alternative embodiment, a viscosity-altering substance 126 may be dried onto a piece of filter paper, which is inserted into the fluid-receiving chamber 114. It should be understood that different amounts or more than one type of viscosity-altering substance 126 may be used in each conduit 112 or fluid-receiving chamber 114. For example, in a heparin/protamine titration analysis of human blood, each conduit 112 may receive a different amount of protamine and, if desired, one or more different viscosity-altering substances (for example, a clotting activator such as tissue thromboplastin) in addition to protamine.

Viscosity-altering substances that act to decrease the tendency of blood to coagulate include, but are not limited to, heparin, warfarin, dicumarol, acenocoumarol, phenprocoumon, diphenadione, phenindione, sodium citrate, citric acid, citrate dextrose, citrate phosphate dextrose, aspirin, and edetate disodium. Viscosity-altering substances that act to increase the tendency of blood to coagulate include, but are not limited to, protamine, platelet-activating factor, factor VIII, factor IX complex, factor XVII, fibrinogen, aminocaproic acid, thrombin, thromboplastin, vitamin K, calcium chloride, kaolin, and diatomaceous earth.

As an example of such usage for a heparin/protamine titration test, in which the fluid sample to be analyzed is heparinized human blood from, for example, a patient undergoing a heart/lung bypass operation, the viscosity-altering substance 126 used is protamine. Protamine is a heparin neutralizer. A certain amount of protamine will neutralize the activity of an equivalent amount of heparin, thereby permitting the heparinized blood to clot. Thus, to prepare a cartridge 100 for a heparin/protamine titration analytical test, a different amount of protamine can be placed onto each of the conduits 112. The amount of protamine used is chosen based on the probable amounts of heparin that exist in the blood sample. For example, cartridges 100 will be available for a broad spectrum of surgical heparin levels. Thus, for example, when a patient is known to have a possible heparin level in his blood of between about 3 units and 5 units, to perform a titration analysis to determine the precise amount of protamine that will be needed to neutralize the heparin in the patient's blood, the range of protamine placed into the conduits 112 may extend from less than about 3 units to more than about 5 units, with each conduit 112 receiving a different amount within that range. The fluid-receiving chamber 114 in which clotting is first observed is that chamber 112 in which the amount of protamine is closest to the amount of heparin activity in the blood that is being circulated.

3. Machine 10

The machine 10 is illustrated in FIGS. 1, 1a, 2, 2a, 3, and 3a. It generally comprises a base 12 having a front portion 14 and a side portion 16. Above the base 12 is an upper portion 18 having a lip 20 to enable the machine 10 to be easily carried by one hand. The upper portion 18 comprises a computer 22 having a touch-sensitive display screen 24, such as that depicted in FIGS. 1 and 3. Contained within the base 12 of the machine 10 is a cartridge holder 302. The cartridge 100 is inserted into the cartridge holder 302 via a slot 26 in the side 16 of the base 12. This slot 26 is alternatively be placed in the front of the machine as shown in FIGS. 1a and 2a. As shown in FIG. 2, the slot 26 is recessed into the side 16 of the machine 10, permitting the cartridge 100 to be grasped by the fingers of the operator and removed. FIG. 13 illustrates in more detail the placement of the cartridge 100 in the machine 10.

In FIG. 13, it can be seen that the cartridge 100, having been inserted into the side 16 of the machine 10 through the slot 26, is secured within the cartridge holder 302 near the front 16 of the base 12 of the machine 10. The injection port 108 of the cartridge 100 is preferably aligned with an aperture 28 in the from 14 of the machine 10 to enable the fluid sample to be introduced into the cartridge 100 after the cartridge 100 is inserted into the machine 10 (see also FIGS. 1 and 2). For the alternative embodiment having the slot 26 in the front of the base 12, no aperture 28 is necessary, and the fluid sample enters directly into the injection port 108. Each air vent/fluid plug device 120 is aligned over a hole 304 in the base of the cartridge holder 302 to permit escape of air that is vented from the cartridge 100 during the movement of the fluid sample into its respective fluid-receiving chamber 114. Preferably, each fluid-receiving chamber 114 is associated with a means for moving the ferromagnetic material (e.g., a washer made of a ferromagnetic material) provided by the machine 10, such as an electromagnet 122, and a means for detecting the position of the ferromagnetic material 116 within the chamber 114, e.g., the detectors 124 depicted in FIGS. 10 and 13. A radio frequency detector may be conveniently employed for this purpose. It should be noted that the detector 124 is not limited to the detection of ferromagnetic material but is capable of detecting any metallic substance placed within the chamber 114. The electromagnet 122 and the position detector 124 are connected to a circuit board 300 through which a computer 22 receives information, provides directions, and provides test results. For simplicity of illustration, only one fluid-receiving chamber 114, corresponding to that shown in FIG. 7, and attendant electromagnet 122 and position detector 124 are shown in FIG. 13. FIG. 10 illustrates a cartridge 100 having four fluid-receiving chambers 114 with the electromagnets 122 above the top 102 of the cartridge 100 and the position detectors 124 below the bottom 104 of the cartridge, in alignment with each chamber 114 and ferromagnetic washer 116.

Operation of the electromagnet 122 is illustrated in FIGS. 12a through 12d. After the fluid 200 has filled the fluid-receiving chamber 114 and reached the air vent/fluid plug device 120 and established a fluid lock, the ferromagnetic washer 116 preferably is at rest on the bottom of the fluid-receiving chamber 114, as shown in FIG. 12a. The electromagnet 122 is then energized and induces the ferromagnetic washer 116 to move to the top of the chamber 114 through the fluid 200 in the manner generally indicated by arrow 202, as illustrated in FIG. 12b. Ater the washer 116 reaches the top of the chamber 114, the electromagnet 122 is turned off and the washer I 16, under the force of gravity, falls through the fluid 200 to the bottom of the chamber 114, as illustrated by arrow 204 in FIG. 12c. The position detector 124 measures the time required for the washer 116 to fall from the top to the bottom of the chamber 114 and sends this information to the computer 22. As the viscosity of the fluid 200 increases, the fall time of the washer 116 increases. Indeed, in the case of blood coagulation, eventually, as shown in FIG. 12d, a washer 116 is unable to move through a blood sample. Alternatively, in another type of analysis, the methods and apparatus of this patent disclosure can be used to measure a decrease in the viscosity of a fluid 200 over time by measuring the decrease in the fall time of the washer 116; for example, this process can be used to measure the effect of coumadin, an anticoagulating drug, on the coagulation of human blood.

When the fluid 200 whose viscosity is being measured is blood, the motion of the washer 116 through the blood also has the effect of activating the clotting process of the blood. This phenomenon might be due to a charge characteristic imparted to the washer 116 by the electromagnet 122. Applicants have also found that the activation effect can be enhanced when the surface of the washer 116 is roughened or when a screen is attached to the washer 116 as shown in FIG. 8b. In both cases, these techniques increase the surface area of the washer. If even faster clotting times are necessary, more than one viscosity-altering substance 126 may be used. For example, a clotting activator such as tissue thromboplastin can be added to the cartridge with the other viscosity-altering substance 126, if any. Similarly, a particulate activator such as diatomaceous earth or kaolin may be used either alone or in combination with a viscosity-altering substance such as protamine or thromboplastin.

The position detector 124 in one of the more preferred embodiments of this invention is a radio frequency detector. Radio frequency detectors sense the position of the washer 116 by sensing the changes in the magnetic field surrounding the detection coil of the radio frequency detector that are caused by the presence of the washer 116. Radio frequency detectors also are preferred for the practice of the present invention because of their sensitivity to ferromagnetic and other metallic materials and resistance to effects caused by other elements of the device, such as the fluid. It should be understood, however, that other types of position detectors 124 are contemplated under the teachings of the present invention.

4. Operation

Figure 11A:
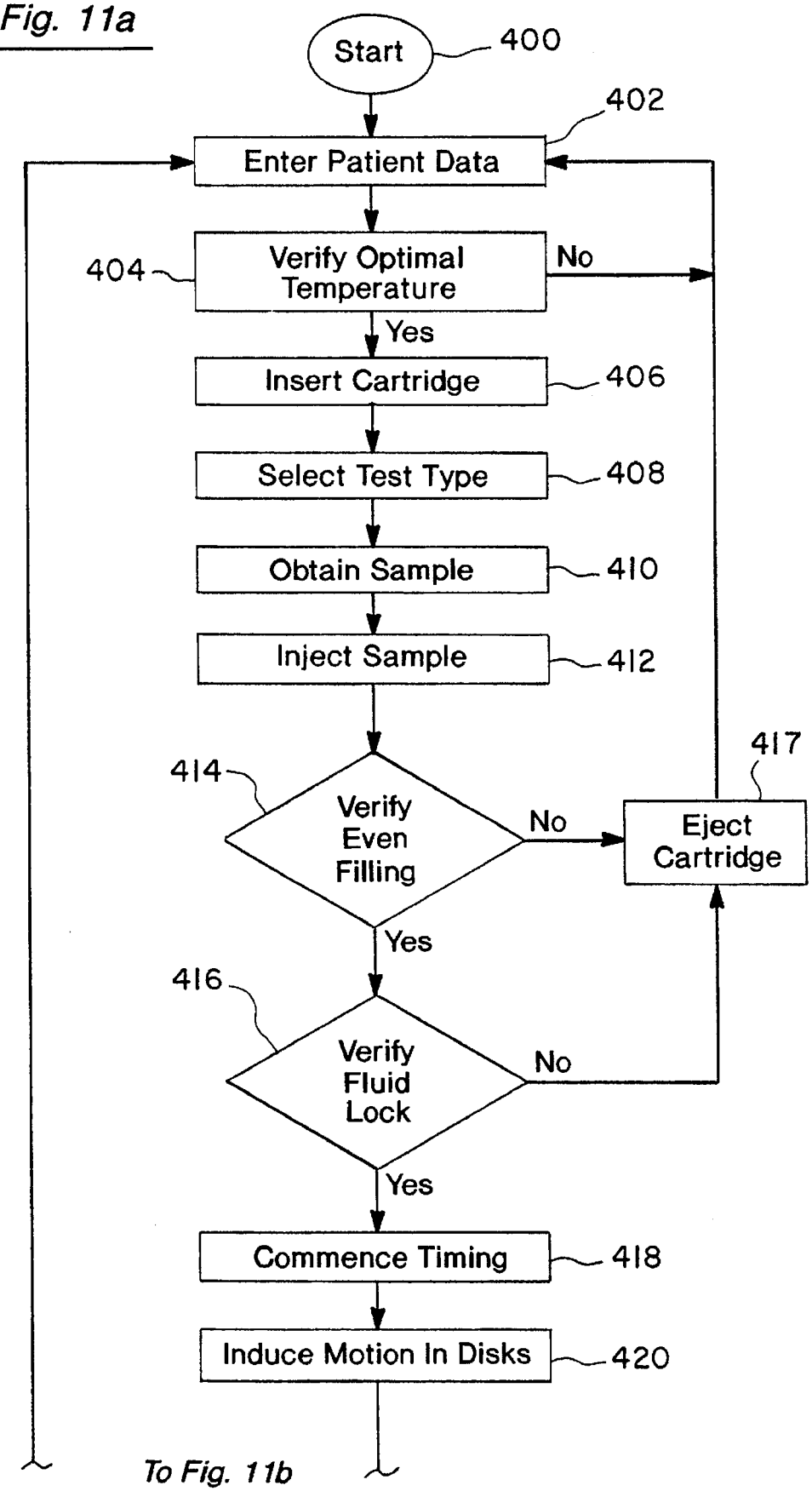
FIG. 11a is a block diagram depicting the sequence of a representative test procedure.
Figure 11B:
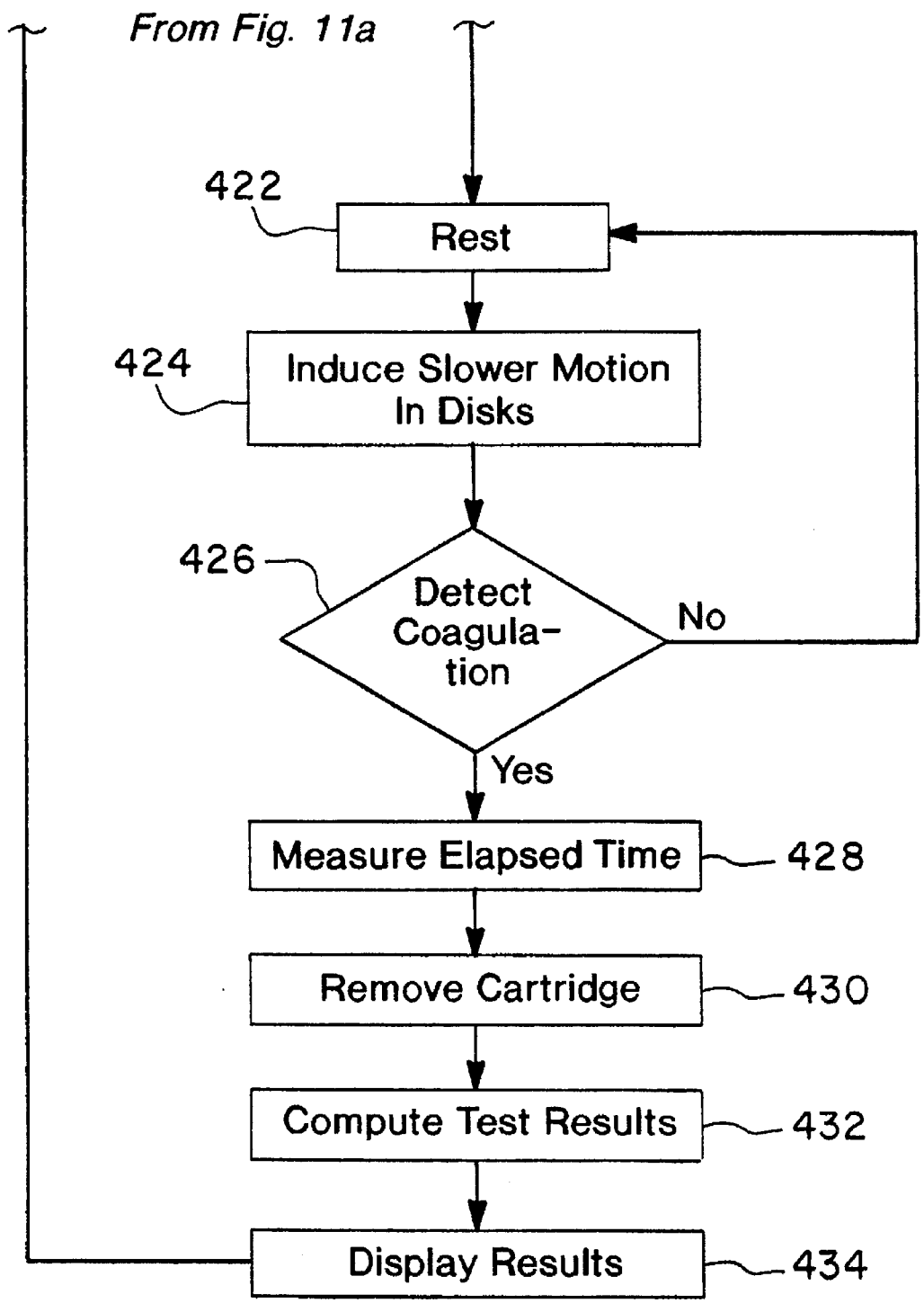

The general operational sequence of the machine 10 with the cartridge 100 is illustrated by FIGS. 11a and 11b. At the commencement 400 of an analytical test, the operator first enters patient data 402 or other information regarding the analytical test, using, for example, a touch-sensitive screen 24 of a computer 22. An optimal temperature of 98.6 degrees Fahrenheit plus or minus 2 degrees Fahrenheit is automatically maintained by the machine 10 during the analytical test. The establishment of the optimal temperature is verified at 404. Should the optimal temperature not be verified, the machine stops the procedure and resets the machine 10. The cartridge 100 is inserted into the machine 10 at 406, and the type of test is selected at 408, either by the operator or automatically by the machine 10 reading a code on the cartridge 100. The operator then obtains the fluid sample at 410 and injects the fluid into the cartridge 100 at 412. Alternatively, for a patient undergoing heart/lung bypass surgery and for whom a heparin/protamine titration analysis is being done, a sample of blood can be obtained from the circuitry of the heart/lung bypass machinery connected to the patient's circulatory system and either manually or automatically introduced into the cartridge 100.

Simultaneous and complete filling of the fluid-receiving chambers 114 is verified by the machine 10 at 414. Should one of the chambers 114 not fill completely, for example, because an air bubble remains in the chamber 114, the machine 10 will eject the cartridge 100 or notify the operator to remove the cartridge 100, as shown at 417. The machine 10 further verifies at 416 that each of the air vent/fluid plug devices 120 has reached fluid lock status, for instance, by detecting visually that the plugs 120 have turned red if blood is the fluid being analyzed. If fluid lock status is not verified, the machine 10 again 417 ejects the cartridge 100. When the cartridge 100 is removed at 417, the machine 10 resets to the position referenced at 402, ready to commence a new test.

Once simultaneous and complete filling of the fluid-receiving chambers 114 and fluid lock are verified, the machine 10 commences measuring the elapsed time at 418 and energizes the electromagnets 122 to rapidly raise the washers 116 several times at 420. This first motion of the washers 116 both further mixes the fluid with any viscosity-altering substance present and, if the fluid is blood, assists in activating clotting, as discussed above. The fluid is then allowed to rest 422 for a short time, after which the machine 10 induces the electromagnets 122 to raise the washers 116 repeatedly at a slower rate, as shown at 424. After each elevation of the washers 116 at 420 and 424, the machine 10 uses the position detectors 124 to detect the time taken for the washers 116 to fall to the bottom of the chambers 114. If an increase in fall time is detected 426 in one or more of the chambers 114, the machine 10 measures the elapsed time between the first raising of the washers 116 and the detection of the increase in fall time 428. Should an increase in fall time not be detected, the machine 10 continues to raise the washers 116 until the end of the period set for the test.

If a change in viscosity is detected in a fluid-receiving chamber 114, the machine 10 measures the elapsed time 428 and the cartridge 100 is removed 430. The computer 22 then computes 432 and displays 434 the test results, subsequently resetting the machine 10 to commence another test 402. It is to be understood that all displayed data, including test results, may be stored in memory, printed, or sent to another computer.

The above disclosure sets forth a number of embodiments of the present invention. Those skilled in this art will however appreciate that other arrangements or embodiments, not precisely set forth, could be practiced under the teachings of the present invention and that the scope of this invention should only be limited by the scope of the following claims.

We claim:

1. An apparatus for detecting changes in viscosity of a fluid, said apparatus comprising:
   a cartridge having a fluid receiving/dispensing reservoir, one or more fluid-receiving chambers, and a plurality of conduits, each of which permits fluid communication between the fluid receiving/dispensing reservoir and each fluid-receiving chamber;
   an injection port in the cartridge for introducing fluid into the fluid receiving/dispensing reservoir;
   a plurality of air vent/fluid plug devices, each of which is in fluid communication with each fluid-receiving chamber;
   a ferromagnetic material that is free to move in each fluid-receiving chamber;
   means for moving the ferromagnetic material in the fluid-receiving chamber; and
   means for detecting a position of the ferromagnetic material in the fluid-receiving chamber.

2. The apparatus of claim 1 wherein a viscosity-altering substance is placed within the cartridge such that fluid introduced into the cartridge will come into contact with the viscosity-altering substance.

3. The apparatus of claim 1 further comprising at least two fluid-receiving chambers for comparing changes in viscosity of the fluid.

4. The apparatus of claim 1 wherein the air vent/fluid plug device vents air displaced from the fluid receiving/dispensing reservoir, the conduit, and the fluid-receiving chamber but prevents fluid from leaving the cartridge via the air vent/fluid plug device.

5. The apparatus of claim 1 wherein the fluid receiving/dispensing reservoir is adapted to dispense fluid simultaneously to more than one fluid-receiving chamber.

6. The apparatus of claim 1 wherein the ferromagnetic material is disk shaped.

7. The apparatus of claim 1 wherein the ferromagnetic material is washer shaped.

8. The apparatus of claim 1 wherein the means for moving the ferromagnetic material is an electromagnet.

9. The apparatus of claim 1 wherein the means for detecting the position of the ferromagnetic material is a radio frequency detector.

10. The apparatus of claim 1 wherein the fluid is human blood.

11. An apparatus for detecting changes in viscosity of human blood, said apparatus comprising:
    a cartridge having a blood receiving/dispensing reservoir, two to six blood-receiving chambers, and a plurality of conduits, each of which permits fluid communication between the blood receiving/dispensing reservoir and each of the blood-receiving chambers;
    an injection port in the cartridge for introducing blood into the blood receiving/dispensing reservoir;
    a plurality of air vent/fluid plug devices, each of which is in fluid communication with each blood-receiving chamber in a manner that permits air to vent from the blood receiving/dispensing reservoir, the conduit, and the blood-receiving chamber as blood is introduced into the blood receiving/dispensing reservoir but prevents blood from leaving the cartridge via the air vent/fluid plug device;
    a ferromagnetic material that is free to move within each of the blood-receiving chambers;
    means for moving the ferromagnetic material within the blood-receiving chambers; and
    means for detecting a position of the ferromagnetic material within the blood-receiving chambers.

12. The apparatus of claim 11 further comprising a viscosity-altering substance placed within the cartridge such that blood introduced into the cartridge will come into contact with the viscosity-altering substance.

13. The apparatus of claim 11 wherein the blood receiving/dispensing reservoir is adapted to dispense blood simultaneously to more than one blood-receiving chamber.

14. The apparatus of claim 11 wherein the ferromagnetic material is disk shaped.

15. The apparatus of claim 11 wherein the ferromagnetic material is washer shaped.

16. The apparatus of claim 11 wherein the means for moving the ferromagnetic material is an electromagnet.

17. The apparatus of claim 11 wherein the means for detecting the position of the ferromagnetic material is a radio frequency detector.

18. An apparatus for detecting changes in viscosity of human blood, said apparatus comprising:
    a cartridge having a blood receiving/dispensing reservoir, two to six blood-receiving chambers, and a plurality of conduits, each of which permits fluid communication between the blood receiving/dispensing reservoir and the blood-receiving chambers, said blood receiving/dispensing reservoir adapted to dispense blood simultaneously to more than one blood-receiving chamber;
    an injection port in the cartridge for introducing blood into the blood receiving/dispensing reservoir;
    a plurality of air vent/fluid plug devices, each of which is in fluid communication with each blood-receiving chamber in a manner that permits air to vent from the blood receiving/dispensing reservoir, the conduit, and each of the blood-receiving chambers as blood is introduced into the blood receiving/dispensing reservoir but prevents blood from leaving the cartridge via the air vent/fluid plug device;
    a blood viscosity-altering substance placed within the cartridge such that blood introduced into the cartridge will come into contact with said blood viscosity-altering substance;
    a ferromagnetic disk that is free to move within each blood-receiving chamber;

an electromagnet for moving the ferromagnetic disk within each blood-receiving chamber; and means for detecting a position of the ferromagnetic disk within each blood-receiving chamber.

19. The apparatus of claim 18 wherein the blood is anticoagulated with an anticoagulant selected from the group consisting of heparin, warfarin, dicumarol, acenocoumarol, phenprocoumon, diphenadione, phenindione, sodium citrate, citric acid, citrate dextrose, citrate phosphate dextrose, aspirin, and edetate disodium.

20. The apparatus of claim 18 wherein the blood viscosity-altering substance is selected from the group consisting of protamine, platelet-activating factor, factor VIII, factor IX complex, factor XVII, fibrinogen, aminocaproic acid, thrombin, thromboplastin, vitamin K, calcium chloride, kaolin, and diatomaceous earth.

21. The apparatus of claim 20 wherein the amount of blood viscosity-altering substance in each of blood-receiving chambers varies.

22. The apparatus of claim 18 wherein the means for detecting the position of the ferromagnetic disk is a radio frequency detector.

23. The apparatus of claim 18 wherein the ferromagnetic disk is washer shaped.

24. A method for detecting changes in viscosity of a fluid, said method comprising the steps of:

(a) heating to an optimal temperature a cartridge having a fluid receiving/dispensing reservoir, one or more fluid-receiving chambers, and a plurality of conduits, each of which permits fluid communication between said fluid receiving/dispensing reservoir and each of said fluid-receiving chambers;

(b) introducing the fluid into the fluid receiving/dispensing reservoir via an injection port in the cartridge;

(c) venting the air displaced from the fluid receiving/dispensing reservoir, conduit, and fluid-receiving chamber via an air vent/fluid plug device that is in fluid communication with each fluid-receiving chamber;

(d) inducing motion in a freely movable ferromagnetic material residing in each fluid-receiving chamber, said ferromagnetic material to detect changes in viscosity of the fluid;

(e) allowing the ferromagnetic material to come to rest for a period; and (f) detecting a position of the ferromagnetic material in the fluid-receiving chamber.

25. The method of claim 24 further comprising repeating steps (d) and (e).

26. The method of claim 24 further comprising preventing the fluid from leaving the cartridge via the air vent/fluid plug device.

27. The method of claim 24 further comprising contacting the fluid with a viscosity-altering substance within the cartridge.

28. The method of claim 24 wherein the motion of the ferromagnetic material is induced through the action of an electromagnet.

29. The method of claim 24 wherein the position of the ferromagnetic material is detected through the action of a radio frequency detector.

30. The method of claim 24 wherein the optimal temperature is 98.6 degrees Fahrenheit plus or minus 2 degrees Fahrenheit.

31. The method of claim 24 wherein the fluid is human blood.

* * * * *